(12) United States Patent
Suh

(10) Patent No.: US 6,280,719 B1
(45) Date of Patent: *Aug. 28, 2001

(54) ANTIFUNGAL BIOCONTROL AGENTS, A PROCESS FOR PREPARING AND TREATING THE SAME

(76) Inventor: Hyung-Won Suh, #311-203, Jugong Apt., Sanggye-dong, Nowon-ku, Seoul 139-200 (KR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/155,650
(22) PCT Filed: Feb. 24, 1998
(86) PCT No.: PCT/KR98/00015
  § 371 Date: Feb. 24, 1999
  § 102(e) Date: Feb. 24, 1999
(87) PCT Pub. No.: WO98/35017
  PCT Pub. Date: Aug. 13, 1998

(30) Foreign Application Priority Data

Feb. 5, 1997 (KR) ............................................. 1997-3568

(51) Int. Cl.[7] .......................... A01N 25/00; A01N 65/00; C07G 17/00; C12N 1/00; C12N 1/20
(52) U.S. Cl. ................... 424/93.43; 424/405; 435/252.4; 435/253.5; 435/267; 435/886
(58) Field of Search .................................. 424/93.43, 405; 435/267, 886, 253.5, 252.4

(56) References Cited

U.S. PATENT DOCUMENTS 5,403,584 * 4/1995 Crawford et al. ................. 424/93.43
5,527,526 * 6/1996 Crawford .......................... 424/93.43

* cited by examiner

*Primary Examiner*—Deborah K. Ware
(74) *Attorney, Agent, or Firm*—Finnegan, Henderson, Farabow, Garrett & Dunner, L.L.P.

(57) ABSTRACT

The present invention relates to antifungal biocontrol agents which enhance plant growth and reduce plant diseases by suppressing fungal pathogens, and the manufacturing and application methods thereof. The antifungal biocontrol agents of the present invention consist of one of the newly isolated strains of Streptomyces sp. WYE 20 (KCTC 0341BP) and WYE 324 (KCTC 0342BP) and a delivery medium which canies and stabilizes the cells. In particular, WYE 20 and WYE 324 of the present invention exhibit strong antifungal activity against *Rhizoctonia solani* and *Phytophthora capsici* and can be used in various ways to reduce fungal diseases in plants such as cucumber (*Cucumis sativus* L.), pepper (*Capsicum annuum* L.), and golf course turfgrasses.

17 Claims, No Drawings

ANTIFUNGAL BIOCONTROL AGENTS, A PROCESS FOR PREPARING AND TREATING THE SAME

This application is a 371 of PCT/KR98/00015 filed Jan. 24, 1998.

FIELD OF THE INVENTION

The present invention relates to antifungal biocontrol agents, and to a process for preparing and treating the same. In particular, the present invention relates to two antifungal biocontrol strains of Streptomyces sp., WYE 20 and WYE 324, capable of enhancing plant growth and reducing plant diseases by suppressing fungal pathogens colonized in rhizosphere soils of host plants, and the preparation method and application method thereof.

BACKGROUND OF THE INVENTION

It is well known that soilborne fungal phytopathogens cause enormous economic losses in the agricultural and horticultural industries. In particular, *Rhizoctonia solani* is one of the major fungal phytopathogens exhibiting strong pathogenicity; it is associated with seedling diseases as well as foliar diseases such as seed rot, root rot, damping-off, leaf and stem rot of many plant species and varieties, resulting in enormous economic losses. For example, *Rhizoctonia solani* AG 1 (IB) causes plant diseases in crops such as cucumber (*Cucmumis sativus* L.) and pepper (*Capsicum annuum* L.) as well as brown patches of golf green creeping bentgrass, *Rhizoctonia solani* AG 2—2 causes large patches in fairway turfgrass on large areas of golf courses resulting in enormous economic losses. In addition, *Phytophthora capsici* is a widespread and highly destructive soilborne fungal phytopathogen that causes root and crown rot as well as the aerial blight of leaves, fruit, and the stems of peppers (*Capsicum annuum* L.). It is very difficult to suppress Phytophthora blight in pepper plants if they are infected by a *Phytophthora capsici*. *Phytophthora capsici* is a particularly destructive phytopathogen responsible for blight of pepper plants during hot and humid rainy seasons resulting in the killing of the pepper plants and consequently enormous economic losses. As mentioned above, both *Rhizoctonia solani* and *Phytophthora capsici* are major fungal phytopathogens which exhibit strong pathogenicity and produce spores which survive for a long time in harsh conditions. Thus, they repeatedly cause plant diseases in large areas when conditions for incidence of the disease are optimal.

Therefore, growers generally apply a mixture of fungicides to plants on a regular basis to control plant diseases caused by both *Rhizoctonia solani* and *Phytophthora capsici*. However, it is becoming increasingly difficult to control Phytophthora blight of pepper plants and Rhizoctonia brown patches of creeping bentgrass because of the emergence of strains of fungal phytopathogens resistant to fungicides. It is also becoming increasingly difficult to control these diseases due to the widespread incidence of *Rhizoctonia solani* resistant to fungicides in golf courses and the proliferation of *Phytophthora capsici* resulting from the successive cultivation of pepper plants.

Intensive use of agrochemicals has also provoked residual toxicity and environmental problems. Furthermore, agrochemicals are considered ineffective in controlling soilborne plant diseases due to wash out, and the lack of an efficient application which allows effective penetration into rhizosphere soils. It is also very difficult to expect long term protection of plants with an application of chemical fungicides. Therefore, using certain rhizosphere bacteria as a biocontrol agent can provide not only more effective and economical practices for the control of plant diseases such as Phytophthora blight caused by *Phytophthora capsici* and golf course turfgrass diseases caused by *Rhizoctonia solani*, but also increased environmental conservation.

It has been shown that use of antagonistic microorganisms is an attractive way to control fungal pathogens (Suh, Ph.D. Dissertation. University of Idaho, Idaho USA. 1992; Crawford et al, Appl. Environ. Microbiol. 59:3899–3905, 1993; U.S. Pat. No. 5,403,584). The inventors disclosed in the prior art that certain Streptomyces species strains can be used to control plant pathogens by using a delivery medium containing peat moss, sand, and cornmeal, in the potting mixture/soil or by coating plant seeds with sodium alginate containing the biocontrol agent, resulting in the colonizing of the roots (U.S. Pat. No. 5,403,584). It has also been disclosed in the prior art that peat containing a beneficial biocontrol agent, can be used to control plant pathogens (U.S. Pat. No. 4,595,589). The delivery medium methods in the prior arts are suitable for the application of seedlings/potting mixtures, but are not quite suitable for direct application to plant seeds or plant roots to achieve efficient protection against fungal phytopathogens.

The object of the present invention is to provide novel strains of Streptomyces species which are capable of controlling fungal phytopathogens by direct application to plant seeds or plant roots utilizing specially designed formulations comprising delivery media containing a biologically pure culture selected fiom the newly isolated strains of Streptomyces species.

Further, it is an object of the present invention to provide antifungal biocontrol agents and describe their use in protecting plants from infections caused by soilborne fungal phytopathogens.

SUMMARY OF THE INVENTION

The present invention has been achieved through the isolation of Streptomyces sp. WYE 20 and WYE 324 which are capable of protecting plants against *Rhizoctonia solani* and *Phytophthora capsici*. The strains, Steptomyces sp. WYE 20 and WYE 324, are effective in preventing the incidence of fungal diseases in plants and in enhancing plant growth in greenhouse and agricultural field trials. Therefore, one aspect of the present invention is microbially pure cultures of Streptomyces sp. WYE 20 and WYE 324.

The present invention also encompasses the various delivery media suitable for the treatment of plant seeds, seedling beds/pots, or potting mixtures/soil with Streptomyces sp. WYE 20 and WYE 324. The delivery medium is very useful for carrying Streptomyces sp. WYE 20 and WYE 324 to inhibit the plant diseases caused by fungal phytopathogens.

In a particular embodiment according to the present invention, the delivery medium consists of wood sawdust, wheat bran, chitin, chitosan, and PHARMAMEDIA (trade name; made by The Budkeye Oilseed Products Company, Texas, USA; aka cottonseed flour having the following components: 59.2% protein, 24.13% carbohydrate, 4.02% fat, 2.55% fiber, and 6.71% ash, as described in the *Manual of Industrial Microbiology and Biotechnology* (1985), by A. L. Demain and N. A. Solomon, editors, p. 130–131.) together with Streptomyces sp. WYE 20 or WYE 324. In another particular embodiment, the delivery medium consists of pectin and colloidal chitin and water together with Streptomyces sp. WYE 20 or WYE 324. In the preferred embodiment, the delivery medium comprises at least 10 colony forming units of Streptomyces sp .WYE 20 or WYE 324 per gram of delivery medium.

The present invention also encompasses methods for reducing fungal infection in seeds, seedlings and/or growing plants prior to or during sowing and growing seasons through the treatment of plant seeds, seedling beds/pots, potting mixture/soils, spraying or in-furrow application.

DETAILED DESCRIPTION OF THE INVENTION

According to the present invention, Streptomyces sp. WYE 20 and WYE 324 are provided that are effective in inhibiting fungal diseases and in enhancing the growth of plants such as pepper, cucumber, and turfgrasses, although their scope is not limited to these examples.

The present invention encompasses the various delivery media that are useful for carrying Streptomyces sp. WYE 20 and WYE 324 to inhibit the plant diseases caused by fungal phytopathogens.

In a particular embodiment of the present invention, the delivery medium consists of 40 to 65 w/w % of wheat bran, 1 to 5 w/w % of chitosan, 30 to 55 w/w % of wood sawdust, 1 to 3 w/w % chitin, and 1 to 3 w/w % of PHARMAMEDIA on the basis of the total weight of the delivery medium. In the preferred embodiment, the delivery medium further consists of 0.2 to 3.5 w/w % of sporulation medium as an additional component on the basis of the total weight of the delivery medium. The preferred sporulation medium is selected from ATCC #5 sporulation medium or yeast extract-glucose-mineral salts, but the presentation does not exclude other sporulation media.

In another particular embodiment, the delivery medium consists of 1.0 to 3.0 w/w % of pectin and 0.1 to 0.6 w/w % of colloidal chitin in water.

In the preferred embodiment, the delivery medium comprises $10^5$ to $10^{10}$, preferably $10^7$ to $10^8$, colony forming units of Streptomyces sp. WYE 20 or WYE 324 per gram of delivery medium.

The present invention includes a process for the production of mycelium and spore inocula of Streptomyces sp. WYE 20 and WYE 324. Viable cells of Streptomyces sp. WYE 20 and WYE 324 are produced by incubating vegetative cells in the yeast extract-glucose-mineral salts or modified bennett liquid medium under the proper conditions.

A process for preparing an antifungal biocontrol agent comprises as follows;

Streptomyces sp. WYE 20 or WYE 324 are prepared by incubating at 130 rpm to 300 rpm, at a temperature of 25° C. to 33° C. for 3 to 7 days.

After harvesting cells of Streptomyces sp. WYE 20 or WYE 324, the cells are lyophilized or mixed directly into a delivery medium.

Further, according to the present invention, a process for preparing an antifungal biocontrol agent comprises the following steps; preparing a delivery medium containing 40 to 65 w/w % of wheat bran, 1 to 5 w/w % of chitosan, 30 to 55 w/w % of wood sawdust, 1 to 3 w/w % of chitin and 1 to 3 w/w % of PHARMAMEDIA on the basis of the total weight of the delivery medium;

autoclaving the resulting delivery medium;

mixing Streptomyces sp. WYE 20 (KCTC 0341BP) or Streptomyces sp. WYE 324 (KCTC 0342BP) with the delivery medium;

incubating incorporated cells of Streptomyces sp. WYE 20 (KCTC 0341BP) or Streptomyces sp. WYE 324 (KCTC 0342BP) at 25° C. to 33° C. for 5–14 days; and aseptically drying the resulting product in a UV light-sterilized laminar flow bench at room temperature to obtain an antifungal biocontrol agent.

Preferably, the process further comprises aseptically blending the resulting dried product.

In the above process, the delivery medium is optionally pelletized and then coated with 0.2 to 3.5 w/w % of sporulation medium on the basis of the total weight of the delivery medium.

Streptomyces sp. WYE 20 or WYE 324 is incorporated to a concentration of $10^5$–$10^{10}$, preferably $10^7$–$10^8$ colony forming unit per gram of delivery medium.

Autoclaving of the delivery medium is carried out at 121° C. for 30 to 40 minutes.

In another embodiment of the present invention, a process is provided for preparing an antifungal biocontrol agent which comprises:

preparing a delivery medium consisting of 1.0 to 3.0 w/w % of pectin and 0.1 to 0.6 w/w % of colloidal chitin in water;

autoclaving the resulting delivery medium; and incorporating Streptomyces sp. WYE 20 (KCTC 0341BP) or Streptomyces sp. WYE 324 (KCTC 0342BP) into the delivery medium.

In the above embodiment of the present invention, Streptomyces WYE 20 or WYE 324 is added to the delivery medium to a final concentration of $10^5$–$10^{10}$, preferably $10^7$–$10^8$ colony forming unit per gram of delivery medium.

Further, the present invention relates to a method for treating the antifungal biocontrol agent which comprises coating, mixing, spraying or in furrow applicating the agent to plant seeds, potting mixture, plants, or soils thereof.

The present invention also relates to an antifungal biocontrol agent which comprises one of the newly isolated strains of Streptomyces sp. WYE 20 and WYE 324. Therefore, it is appreciated that an antifungal biocontrol agent containing microorganisms having an antifungal property equal to that of the strains together with the delivery medium according to the present invention is within the true spirit and scope of the present invention. The present invention will be further described in the following examples. However, the present invention is not limited to the following examples.

Materials and Methods

1. Culture Medium of Microorganism

All bacterial culture media used distilled water and were sterilized by autoclaving prior to use. All bacterial samples were treated by standard aseptic laboratory techniques to maintain purity.

1) CYD (casamino acid/yeast extract/dextrose/agar) medium contains casamino acids (DIFCO: 0.5 g/l), yeast extract (DIFCO: 0.8 g/l), D-glucose (0.4 g/l), $K_2HPO_4$ (2.0 g/l; pH 7.2–7.4), and agar (18 g/l) in distilled water.

2) WYE (water/yeast extract/agar) medium, modified from Reddi and Rao (1971) contains yeast extract (0.25 g/l), $K_2HPO_4$ (2.0 g/l; pH 7.2–7.4) and agar (18 g/l) in distilled water.

3) YGM (yeast extract/glucose/mineral salts) medium comprises 0.6% (w/v) yeast extract (DIFCO Laboratories, Detroit. Mich. U.S.A.). 1.0% (w/v) glucose, and phosphate mineral salt solution (5.3 g of $Na_2HPO_4$, 1.98 g of $KH_2PO_4$, 0.2 g of $MgSO_4$ $7H_2O$, 0.2 g of NaCl, 0.05 g of $CaCl_2$ $2H_2O$, plus 1.0 ml of trace elements (Pridham and Gottlieb, J. Bacteriology 56:107–114, 1948) per liter of deionized H2O; pH 7.1 to 7.2). The solution of trace elements consists of 0.64 g of $CuSO_4$ $5H_2O$, 0.11 g of $FeSO_4$ $7H_2O$. 0.79 g of $MnCl_2$ $4H_2O$, 0.15 g of $ZnSO_4$ $7H_2O$ in 100 ml of distilled water.

4) CM (chitin/mineral salts/agar) medium comprises 0.4% to 0.6% (w/v) colloidal chitin prepared by the previously known method (Hsu and Lockwood, Applied Microbiology, p422–426, 1975), 0.6% (w/v) $(NH_4)_2SO_4$, and 2.0% (w/v) agar per liter of phosphate mineral salt solution described above; pH 7.0 to 7.2.

5) Laminarin agar medium comprises 0.25% (w/v) laminarin, 0.6% (w/v) $(NH_4)_2SO_4$, and 2.0% (w/v) agar per liter of phosphate mineral salt solution described above; pH 7.2 to 7.4.

6) Modified Bennett liquid medium contains yeast extract (2 g/l), beef extract (2 g/l), peptone (2 g/l), glucose (10 g/l), and nystatin (5 µg/ml; pH 6.5–7.5) in distilled water.

7) Modified Bennett Agar medium contained yeast extract (2 g/l), beef extract (2 g/l), peptone (2 g/l), glucose (10 g/l), nystatin (5 µg/ml; pH 6.5–7.5), and agar (20 g/l) in distilled water.

8) ISP medium #2 (DIFCO).
9) ISP medium #3 (DIFCO).
10) ISP medium #4 (DIFCO).

11) Sporulation medium (ATCC medium #5) contains yeast extract (1.0 g/l), beef extract (1.0 g/l), tryptose (2.0 g/l), $FeSO_4$(0.01 g/l), glucose (1.0 g/l), and agar (15 g/l) (17th Edition ATCC Catalogue of Bacteria and Bacteriophages).

2. Identification of Streptomyces sp. WYE 20 and WYE 324

Strains WYE 20 and WYE 324 were identified as Streptomyces species on the basis of the morphological, physiological, and chemical characteristics of the genus Streptomyces, as defined in Bergey's Manual of Systematic Bacteriology (1989); the International Streptomyces Project (ISP) (1974)); and Williams, et al. (1983). The summarized results of these strains in the respects of morphological, physiological, and chemical characteristics are reported in Tables I to V.

3. Preparation of Seed Culture and Storage of Streptomyces sp. WYE 20 and WYE 324

Spores from a CYD agar slant were inoculated with an inoculation loop into 500 ml flasks containing 50 ml of modified bennett liquid medium (pH 6.5–7.5). The medium was sterilized by autoclaving for 15 minutes at 121° C. prior to inoculation. The inoculated flasks were then incubated with shaking at 130 to 300 rpm at 25° C. to 33° C. for 1–4 days to provide a standard inoculum.

For short-term use, Streptomyces sp. WYE 20 and WYE 324 were incubated on CYD or WYE agar slant at 25° C. until sporulated and then stored at 4° C. until used. The cultures were transferred every 4 weeks. Spores suspended in autoclaved glycerol (15%–30%) (121° C. 15 minutes) were used for long-term storage at −70° C.

4. Harvesting and Production of Mycelia and Spores in Liquid Culture

One liter flasks containing 200 ml of modified bennett liquid medium or 200 ml of YGM (pH 6.5–7.5) medium were inoculated with 8 ml of each seed culture for the production of viable cells of mycelia and spores of Streptomyces sp. WYE 20 and WYE 324. The inoculated flasks were incubated with shaking at 130 to 300 rpm at 25° C. to 33° C. for 3 to 7 days. Viable cells of mycelia and spores produced through the above process were aseptically harvested by centrifugation at 4,000 rpm for 10 minutes.

5. Production of Viable Cells of Mycelia and Spores with Delivery Medium and Preparation of Antifungal Biocontrol Agent.

(1) Preparation of antifungal biocontrol agent in the form of powder comprising Streptomyces sp. WYE 20 or WYE 324 and a delivery medium.

The delivery medium of the present invention which consisted of wheat bran of 40 to 65 w/w %, chitosan of 1 to 5 w/w %, wood sawdust of 30 to 55 w/w %, chitin of 1 to 3 w/w %, PHARMAMEDIA (The Budkeye Oilseed Products Company, Fortworth, Tex., U.S.A.) of 1 to 3 w/w % on the basis of the total weight of the medium was thoroughly mixed. The resulting delivery medium was pelletized and spray-coated with sporulation medium (ATCC #5 or YGM medium) of 0.2 to 3.5 w/w %, and then autoclaved at 121° C. for 30 to 40 minutes. There was no effect on cellular growth when the sporulation medium was added below 0.2 w/w %, whereas the initial cellular growth was retarded when the sporulation medium was added over 3.5 w/w %.

One hundred to two hundred ml of Streptomyces sp. WYE 20 and WYE 324 ($10^5$–$10^7$ cfu/ml) were inoculated into the resulting autoclaved delivery medium and then incubated at 30° C. for 5 to 14 days. Streptomyces sp. WYE 20 and WYE 324 in the delivery medium were aseptically harvested and dried in U.V.-sterilized laminar flow bench. The dried product was aseptically blended to obtain an antifungal biocontrol agent comprising Streptomyces sp. WYE 20 or WYE 324 and the delivery medium.

(2) Preparation of antifungal biocontrol agent comprising Streptomyces sp. WYE 20 or WYE 324 and a liquid delivery medium.

Preparation of the antifungal biocontrol agent was carried out by incorporating viable cells of mycelia and spores of Streptomyces sp. WYE 20 or WYE 324 obtained in the above into autoclaved delivery medium of 1.0 to 3.0 w/w % of pectin and 0.1 to 0.6 w/w % of colloidal chitin in water.

6. Fungal Pathogens

The following fungal pathogens were used for an antifungal test: *Pythium ultimum, Pythium graminicola, Rhizoctonia solani, Rhizoctonia solani* AG 1 (IB), *Rhizoctonia solani* AG 2—2 (IV), *Fusarium oxysporum, Fusarium sambucinctum, Fusarium solani, Phytophthora capsici, Phytophthora parasitica, Sclerotinia sclerotiorum, Sclerotium cepivoruim*, and *Verticillium dahliae*. All strains were grown on potato dextrose agar (DIFCO) or corn meal agar (DIFCO) at 25° C. and stored at 4° C.

7. Determination of Cell Number in Delivery Medium

One gram of delivery medium containing Streptomyces sp. WYE 20 or WYE 324 was added to 9 ml of sterile distilled water and thoroughly mixed with VORTEX™. The resulting suspension was serially diluted and spread on CMA plates to determine colony forming unit (cfu) per gram. The plates were incubated at 30° C. and colony formation was observed. The same method was used to determine cfu/ml of delivery medium in the form of liquid.

8. In Vivo Bioassay to Determine Antifungal Activity of Streptomyces sp. WYE 20 and WYE 324

The activity of Streptomyces sp. WYE 20 or WYE 324 to enhance plant growth and to reduce plant diseases caused by fungal pathogens was determined by treating cucumber, pepper, or golf course turfgrasses with Streptomyces sp. WYE 20 or WYE 324 in a delivery medium, and then planting treated and untreated seeds in a suitable growing medium or agricultural fields. The activity of Streptomyces sp. WYE 20 or WYE 324 in a delivery medium as a biocontrol agent was measured in terms of emergence, outgrowth of emerged plants, plant height, and capability of disease control.

EXAMPLE I

Isolation of Streptomyces sp. WYE 20 and WYE 324

Microbial strains having excellent antifungal activity are used for the production of antifungal biocontrol agents of this present invention. In order to obtain and isolate such strains, rhizopheric soil samples of pepper plants were collected from four different sites in Goesan, Chungbuk Province, Korea.

Purification of the isolated colonies was carried out by subculturing and incubating the strains on WYE agar plates at 25° C. for 4 to 10 days to allow the strains to sporulate. Then, their colonies were isolated and streaked onto new WYE agar plates to obtain pure cultures. Pure cultures were transferred to CYD agar slants, incubated at 25° C.–30° C. until sporulated, and stored at 4° C. The cultures were transferred every 4 weeks. The obtained strains were tested with respect to antagonistic activity against *Rhizoctonia solani* and *Phytophthora capsici*; enzyme activities exhibiting fungal cell wall degradation; root colonization, growth at a low temperature (4° C., 8° C.).

EXAMPLE II

Identification and Characterization of Streptomyces sp. WYE 20 and WYE 324

The morphological, physiological, and chemical characteristics of microorganisms obtained in Example I were investigated on the basis of Bergey's Manual of Systematic Bacteriology (1989). The results are shown in Tables I to V.

TABLE I

| Medium | Cellular Growth WYE 20 | Cellular Growth WYE 324 | Aerial Mycelium WYE 20 | Aerial Mycelium WYE 324 | Substrate Mycelium WYE 20 | Substrate Mycelium WYE 324 | Color of Spore Mass WYE 20 | Color of Spore Mass WYE 324 |
|---|---|---|---|---|---|---|---|---|
| ISP #2 | Good | Good | Abundant | Abundant | Light Yellow | Light Yellow | Grayish Pink | Grayish Pink |
| ISP #3 | Good | Good | Abundant | Abundant | Pale Yellow | Pale Yellow | Grayish Pink | Grayish Pink |
| ISP #4 | Good | Good | Abundant | Abundant | Pale Yellow | Pale Yellow | Grayish Pink | Grayish Pink |

TABLE IIa

| Characteristics | Strain WYE 20 | Strain WYE 324 |
|---|---|---|
| Spore chain morphology | Spirales | Spirales |
| Spore chain ornamentation | Smooth | Smooth |
| Spore shape | Cylinderical | Cylinderical |
| Diffusible pigments | − | − |
| Melanin production | + (brown-dark brown) | + (brown-dark brown) |
| Antimicrobial activity: | | |
| *Aspergillus niger* | + | + |
| *Bacillus subtilis* NCIB 3610 | + | + |
| *Streptomyces murinus* | + | + |
| *Candida albicans* | − | − |
| *Saccharomyce cerevisiae* CBS 1172 | − | − |
| *Micrococcus luteus* NCIB 196 | + | + |
| Lecithinase activity | + | + |
| Pectin hydrolysis | − | − |
| Skim milk hydrolysis | + | + |
| Starch hydrolysis | + | + |
| Nitrate reduction | + | + |
| $H_2S$ production | $+^{4week}$ | − |
| Antibiotic resistance (μg/ml): | | |
| Oleandomycin (100) | $-^{1\ mm\ giz}$ | $-^{1\ mm\ giz}$ |
| Neomycin (50) | + | + |
| Rifampicin (50) | $-^{2\ mm\ giz}$ | − |
| Lincomycin (100) | + | + |
| Novobiocin (100) | − | − |
| Ganamycin (100) | $-^{2\ mm\ giz}$ | $-^{3\ mm\ giz}$ |
| Ampicilin (100) | + | + |
| Streptomycin (100) | $-^{3\ mm\ giz}$ | $-^{2\ mm\ giz}$ |
| Kasugomycin (100) | + | $-^{1\ mm\ giz}$ |
| Tetracycline (100) | + | + |
| Chloramphenicol (100) | − | $-^{3\ mm\ giz}$ |

−: growth inhibition zone (giz) > 4 mm
+: no growth inhibition zone

TABLE IIb

| Characteristics | Strain WYE 20 | Strain WYE 324 |
|---|---|---|
| Degradation activity: | | |
| Xanthine | − | − |
| Elastin | + | + |
| Arbutin | − | − |
| Xylan | + | + |
| L-tyrosine | + | + |
| Allantoin | + | + |
| Growth at 45° C. | − | − |
| Growth at pH 4.3 | − | − |
| Growth in the presence of chemical inhibitors (%, w/v): | | |
| NaCl (7.0) | − | − |
| Sodium azide (0.01) | − | − |
| Phenol (0.1) | + | + |
| Potassium tellurite (0.001) | + | + |
| Crystal violet (0.0001) | + | − |
| Neolin (0.5) | + | + |
| Neolin (1.0) | + | + |
| Tween 20 (0.5) | + | + |
| Tween 20 (1.0) | + | + |
| RIZORAX ™ (0.1) | + | + |
| RIZORAX ™ (1.0) | + | + |
| GOCHUTAN ™ (0.1) | + | + |
| SMIRAX ™ (0.1) | − | − |
| LIDOMIL MG ™ (0.125) | + | ± |
| LIDOMIL MG ™ (0.25) | − | − |
| ANGCOL ™ (0.1) | − | − |
| Nitrogen utilization (0.1% w/v): | | |
| L-asparagine | + | + |
| DL-α-amino-n-butyric acid | − | − |

TABLE IIb-continued

| Characteristics | Strain WYE 20 | Strain WYE 324 |
|---|---|---|
| L-cysteine | ± | + |
| L-valine | ± | + |
| L-phenylalanine | − | ± |
| L-histidine | + | + |
| L-hydroxyproline | + | + |
| L-arginine | + | + |
| L-methionine | ± | + |
| Potassium nitrate | − | − |
| L-serine | + | + |
| L-threonine | + | + |

™Trade mark

TABLE IIc

| Characteristics | Strain WYE 20 | Strain WYE 324 |
|---|---|---|
| Carbon utilization (1.0% w/v): | | |
| Sucrose | + | + |
| Meso-inositol | − | − |
| Mannitol | − | − |
| L-Rhamnose | + | − |
| Raffinose | − | − |

TABLE IIc-continued

| Characteristics | Strain WYE 20 | Strain WYE 324 |
|---|---|---|
| D-Melezitose | + | + |
| Adonitol | − | − |
| D-Melibiose | ± | ± |
| Dextran | ± | − |
| Xylitol | ± | − |
| L-Arabinose | ± | ± |
| D-Fructose | + | + |
| D-Galactose | + | + |
| D-Glucose | + | + |
| D-Salicin | ± | + |
| D-Xylose | + | + |
| Sorbose | + | + |
| D-Lactose | + | + |
| D-Mannose | + | + |
| Trehalose | + | + |
| Maltose | + | + |
| Cellobiose | + | + |
| Inulin | − | − |
| Sodium acetate (0.1) | + | + |
| Sodium citrate (0.1) | + | + |
| Sodium malonate (0.1) | ± | ± |
| Sodium propionate (0.1) | + | + |
| Sodium pyruvate (0.1) | + | + |
| Diaminopimelic acid | LL | LL |

TABLE III

| | Streptomyces sp. WYE 20 Content (%) | | | | | | |
|---|---|---|---|---|---|---|---|
| Fatty acid | 1 | 2 | 3 | 4 | Minimum | Maximum | Average |
| Saturated fatty acid | | | | | | | |
| 14:0 | 0.33 | 0.30 | 0.53 | 0.53 | 0.30 | 0.53 | 0.42 |
| 15:0 | 1.52 | 1.54 | 1.13 | 1.19 | 1.13 | 1.54 | 1.35 |
| 16:0 | 5.09 | 5.22 | 5.95 | 6.03 | 5.09 | 6.03 | 5.57 |
| 17:0 | 0.30 | 0.31 | — | — | nd | nd | nd |
| Unsaturated fatty acid | | | | | | | |
| 16:1 cis 9 | 6.42 | 6.25 | 5.45 | 5.80 | 5.45 | 6.42 | 5.98 |
| 17:1 cis 9 | 1.08 | 1.06 | 0.65 | 0.63 | 0.63 | 1.08 | 0.86 |
| Methyl group branch | | | | | | | |
| 13:0 anteiso | 0.14 | 0.14 | — | — | nd | nd | nd |
| 14:0 iso | 1.30 | 1.23 | 2.40 | 2.26 | 1.23 | 2.40 | 1.80 |
| 15:0 iso | 7.19 | 7.09 | 7.58 | 7.21 | 7.09 | 7.58 | 7.27 |
| 15:0 anteiso | 27.95 | 27.48 | 30.94 | 32.13 | 27.48 | 32.13 | 29.63 |
| 16:1 iso H | 2.80 | 2.69 | 3.01 | 2.98 | 2.69 | 3.01 | 2.87 |
| 16:0 iso | 15.01 | 15.17 | 17.71 | 17.09 | 15.01 | 17.71 | 16.25 |
| 16:0 9? $CH_3$ | 3.42 | 3.42 | 2.77 | 2.69 | 2.69 | 3.42 | 3.08 |
| 17:1 anteiso C | 7.24 | 7.25 | 5.56 | 5.82 | 5.56 | 7.25 | 6.47 |
| 17:0 iso | 1.83 | 1.93 | 1.85 | 1.65 | 1.65 | 1.93 | 1.82 |
| 17:0 anteiso | 11.78 | 12.35 | 10.77 | 10.63 | 10.63 | 12.35 | 11.38 |
| 17:0 10 $CH_3$ | 0.23 | 0.27 | — | — | nd | nd | nd |
| 18:1 iso H | 0.99 | 1.02 | 0.62 | 0.59 | 0.59 | 1.02 | 0.81 |
| Hydroxyl group branch | | | | | | | |
| 17:0 iso 2OH | 0.40 | 0.41 | — | — | nd | nd | nd |
| 17:0 3OH | 0.27 | 0.32 | — | — | nd | nd | nd |
| Cyclopropane | | | | | | | |
| 17:0 Cyclopropane | 3.30 | 3.27 | 2.30 | 2.23 | 2.23 | 3.30 | 2.78 |
| Unknown 17.595 SM | 0.78 | 0.82 | 0.50 | 0.55 | 0.50 | 0.82 | 0.66 |

Note:
The first and second time: Cells grown in Trypticase Soy Broth (TSB).
The third and fourth time: Cells grown on Trypticase Soy Agar (TSA).
—: no detection.
nd: not determined.

TABLE IV

| | Streptomyces sp. WYE 324 Content (%) | | | | | | |
|---|---|---|---|---|---|---|---|
| Fatty acid | 1 | 2 | 3 | 4 | Minimum | Maximum | Average |
| Saturated fatty acid | | | | | | | |
| 14:0 | 0.28 | 0.26 | 0.42 | 0.45 | 0.26 | 0.45 | 0.35 |
| 15:0 | 2.22 | 2.19 | 1.23 | 1.25 | 1.23 | 2.22 | 1.72 |
| 16:0 | 4.34 | 4.40 | 5.89 | 6.19 | 4.34 | 6.19 | 5.21 |
| 17:0 | 0.40 | 0.43 | — | — | nd | nd | nd |
| Unsaturated fatty acid | | | | | | | |
| 15:1 B | 0.20 | 0.15 | — | — | nd | nd | nd |
| 16:1 cis 9 | 6.40 | 6.39 | 5.66 | 5.54 | 5.54 | 6.40 | 6.00 |
| 17:1 cis 9 | 1.40 | 1.43 | 0.78 | 0.71 | 0.71 | 1.43 | 1.08 |
| Methyl group branch | | | | | | | |
| 13:0 iso | 0.08 | 0.10 | — | — | nd | nd | nd |
| 13:0 anteiso | 0.13 | 0.14 | — | — | nd | nd | nd |
| 14:0 iso | 1.64 | 1.62 | 2.18 | 2.30 | 1.62 | 2.30 | 1.94 |
| 15:0 iso | 7.48 | 7.48 | 8.15 | 8.10 | 7.48 | 8.15 | 7.80 |
| 15:0 anteiso | 30.25 | 30.10 | 31.65 | 31.76 | 30.10 | 31.76 | 30.94 |
| 16:1 iso H | 2.59 | 2.57 | 3.34 | 3.23 | 2.57 | 3.34 | 2.93 |
| 16:0 iso | 14.05 | 14.06 | 16.67 | 16.69 | 14.05 | 16.69 | 15.37 |
| 16:0 9? $CH_3$ | 3.56 | 3.56 | 3.29 | 3.12 | 3.12 | 3.56 | 3.38 |
| 17:1 anteiso C | 6.68 | 6.65 | 5.97 | 5.90 | 5.90 | 6.68 | 6.30 |
| 17:0 iso | 1.77 | 1.82 | 2.14 | 2.16 | 1.77 | 2.16 | 1.97 |
| 17:0 anteiso | 10.78 | 10.95 | 10.68 | 10.72 | 10.68 | 10.95 | 10.78 |
| 17:0 10 $CH_3$ | 0.18 | 0.18 | — | — | nd | nd | nd |
| 18:1 iso H | 0.49 | 0.50 | — | — | nd | nd | nd |
| Hydroxyl group branch | | | | | | | |
| 17:0 iso 2OH | 0.50 | 0.51 | — | — | nd | nd | nd |
| 17:0 3OH | 0.24 | 0.19 | — | — | nd | nd | nd |
| Cyclopropane | | | | | | | |
| 17:0 Cyclopropane | 3.15 | 3.14 | 1.95 | 1.89 | 1.89 | 3.15 | 2.53 |
| Unknown 17.595 SM | 0.68 | 0.69 | — | — | nd | nd | nd |

Note: The first and second time: Cells grown in Trypticase Soy Broth (TSB).
The third and fourth time: Cells grown on Trypticase Soy Agar (TSA).
—: no detection. nd: not determined.

TABLE V

| Characteristics | Streptomyces sp. WYE 20 | Streptomyces colombiensis ATCC 27425 | Streptomyces sp. WYE 324 | Streptomyces goshikiensis ATCC 23914 |
|---|---|---|---|---|
| Spore chain: Rectiflexibles | − | + | − | − |
| Spore chain: Retinaculiaperti | − | − | − | − |
| Spore chain: Spirales | + | + | + | + |
| Spore chain: Verticillati | − | − | − | − |
| Spore surface ornamentation: Smooth | + | + | + | + |
| Spore surface ornamentation: Rugose | − | − | − | − |
| Color of spore mass: Red | − | + | − | + |
| Color of spore mass: Gray | − | − | − | − |
| Color of spore mass: Green | − | − | − | − |
| Diffusible pigment: Red/Orange | − | − | − | − |
| Diffusible pigment: Yellow/Brown | − | − | − | − |
| Melanin production | + | + | + | + |
| Fragmentation | − | − | − | − |
| Use of DL-α-amino-n-butyric acid (0.1%, w/v) | − | − | − | − |
| Use of L-histidine (0.1%, w/v) | + | − | + | − |
| Use of L-hydroxyproline (0.1%, w/v) | + | + | + | − |
| Lecithinase activity | + | + | + | + |
| Pectin hydrolysis | − | − | − | − |
| Nitrate reduction | + | + | + | + |
| H2S Production | + | + | − | − |
| Bacillus subtilis NCIB | + | + | + | + |
| Streptomyces murinus | + | + | + | + |
| Aspergillus niger | + | + | + | + |
| Xanthin degradation activity | − | + | − | + |
| Allantoin degradation activity | + | + | + | + |
| Arbutin degradation activity | − | + | − | − |

TABLE V-continued

| Characteristics | Streptomyces sp. WYE 20 | Streptomyces colombiensis ATCC 27425 | Streptomyces sp. WYE 324 | Streptomyces goshikiensis ATCC 23914 |
|---|---|---|---|---|
| Neomycin (50 μ g/ml) resistance | + | + | + | + |
| Rifampicin (50 μ g/ml) resistance | − | − | − | − |
| Growth at 45° C. | − | − | − | − |
| Growth at NaCl (7%, w/v) | − | − | − | − |
| Growth at sodium azide (0.01%, w/v) | − | − | − | − |
| Growth at phenol (0.1%, w/v) | + | + | + | + |
| Utilization of D-xylose (1.0%, w/v) | + | − | + | − |
| Utilization of meso-inositol (1.0%, w/v) | − | − | − | − |
| Utilization of mannitol (1.0%, w/v) | − | − | − | − |
| Utilization of D-fructose (1.0%, w/v) | + | + | + | + |
| Utilization of L-rhamnose (1.0%, w/v) | + | − | − | − |
| Utilization of raffinose (1.0%, w/v) | − | − | − | − |
| Utilization of innulin (1.0%, w/v) | − | − | − | − |
| Utilization of adonitol (1.0%, w/v) | − | − | − | − |
| Utilization of cellobiose (1.0%, w/v) | + | + | + | + |

The two strains obtained in Example I were identified as the genus Streptomyces, as a result of analyzing the data of Tables I to V on the basis of Bergey's Manual of Systematic Bacteriology (1989); International Streptomyces Project (ISP) (1974)); and William et al (1983).

The two strains were named as WYE 20 and WYE 324, respectively. The train WYE 20 might belong to the species *Streptomyces colombiensis* or a closely related species in cluster 61 on the basis of the morphological, physiological, and chemical characteristics of the genus Streptomyces, but the strain was identified as a novel strain of the genus Streptomyces. Strain WYE 324 might belong to the species *Streptomyces goshikiensis* or a closely related species in cluster 61 on the basis of the morphological, physiological, and chemical characteristics of the genus Streptomyces, but the strain was identified as a novel strain of the genus Streptomyces.

The strains WYE 20 and WYE 324 were deposited in the Korean Culture Type Collection (KCTC). Korea Research Institute of Bioscience and Biotechnology located at #53, Oun-dong, Yusong-ku, Taejon, Korea on Jun. 18, 1997 under the Budapest Treaty on the International Recognition of the Deposit of Microorganisms for the Purpose of Patent Procedure, assigned with the Accession No. KCTC 0341BP (WYE 20) and KCTC 0342BP (WYE 324), respectively.

EXAMPLE III

Optimum Temperature for The Cellular Growth of Streptomyces sp. WYE 20 and WYE 324

To investigate the effect of temperature on the growth of the Streptomyces sp. WYE 20 and WYE 324, spores of strains WYE 20 and WYE 324 were streak-inoculated on modified bennett agar plates. The streaked plates were incubated at predetermined temperatures of 4° C., 8° C., 27° C., 37° C., and 45° C. for 3 weeks. The growth was recorded at 7, 14, and 21 days. The results are shown as good growth (+); slow growth (±); no growth (−) in Table VI.

TABLE VI

| Strain | 4° C. | | 8° C. | | 27° C. | | 37° C. | | 45° C. | |
|---|---|---|---|---|---|---|---|---|---|---|
| | 7 days | 21 days | 7 days | 14 days | 7 days | 14 days | 7 days | 14 days | 7 days | 14 days |
| WYE 20 | ± | + | + | + | + | + | ± | + | − | − |
| WYE 324 | − | ± | ± | + | + | + | ± | + | − | − |

As shown in Table VI, strain WYE 20 represented slow growth after a week of incubation at 4° C. and good growth after 3 weeks' incubation, whereas strain WYE 324 represented slow growth after 3 weeks incubation at 4° C. Strain WYE 20 represented good growth at both 8° C. and 27° C. However, strain WYE 324 represented slow growth after a week of incubation at 8° C. and represented good growth after 2 weeks' incubation at 8° C. In addition, strain WYE 324 represented good growth at 27° C. Strains WYE 20 and WYE 324 represented slow growth after a week of incubation at 37° C. and represented good growth after 2 weeks incubation at 37° C., but they did not grow at 45° C.

EXAMPLE IV

Enzyme Activity and Antagonism Assay (1) Enzyme Activity Assay

To assay the enzyme activity of the strains WYE 20 and WYE 324, both chitinase and β-1,3-glucanase were used which were known as enzymes capable of parasitizing/inhibiting fungal pathogens.

In order to determine the chitinase activity of strains WYE 20 and WYE 324, each strain was streaked on CM agar plates which contained colloidal chitin as a sole carbon source, and then incubated at 30° C. for 14 days. Colony formation and growth were observed. The strains WYE 20 and WYE 324 were proved to have a chitinase activity from the above.

To determine β-1,3-glucanase activity of the strains WYE 20 and WYE 324, each strain was streaked on laminarin agar plates which contained laminarin as a sole carbon source, and then incubated at 27° C. for 7 days. Colony formation and growth were observed. The strains WYE 20 and WYE 324 were proved to have a β-1,3-glucanase activity from the above.

(2) Antagonism Assay

An in vitro plate assay was performed to test the antagonistic activity of strains WYE 20 and WYE 324 in terms of growth inhibition of fungal phytopathogens. Each strain was streak-inoculated on CMA plates and incubated at 30° C. for 6 to 10 days. A PDA (Potato Dextrose Agar) block containing actively growing fungal mycelia was then aseptically placed in the center of the plate and incubated at 25° C. for 24 to 192 hours. The above PDA block was inoculated into CMA plates not containing strain WYE 20 or WYE 324 and used as a control. The bioassay was replicated on three plates. The antagonism was recorded as a degree of inhibition of mycelial growth of fungal pathogens as shown in Table VII.

TABLE VII

| Fungal Pathogens | Antagonistic activity | |
|---|---|---|
| | WYE 20 | WYE 324 |
| Pythium ultimum[1] | + | + |
| Pythium graminicola[2] | ++ | ++ |
| Fusarium oxysporum | ++ | ++ |
| Fusarium sambucinctum | ++ | nt |
| Fusarium solani | ++ | ++ |
| Rhizoctonia solani | ++ | ++ |
| Rhizoctonia solani AG 1 (IB) | ++ | ++ |
| Rhizoctonia solani AG 2-2 (IV) | ++ | ++ |

TABLE VII-continued

| Fungal Pathogens | Antagonistic activity | |
|---|---|---|
| | WYE 20 | WYE 324 |
| Phytophthora capsici | ++ | ++ |
| Phytophthora parasitica | ++ | ++ |
| Sclerotinia sclerotiorum | ++ | ++ |
| Sclerotium cepivorum[3] | ++ | ++ |
| Verticillium dahliae[3] | ++ | nt |

[1]24 hour incubation, [2]36 hour incubation, [3]192 hour incubation.
Remnant: 96 hour incubation
++: Strong inhibition with zone of inhibition ≥ 1.0 cm
+: Growth definitely retarded, with obvious zone of inhibition near colony
−: Not antagonistic, or very weakly antagonistic.
nt: not tested.

As shown in Table VII, strains WYE 20 and WYE 324 showed an obvious zone of inhibition against *Pythium ultimum*. Strain WYE 20 showed strong antagonism against *Pythium grominicola, Fusarium oxysporum, Fusarium sambucinctum, Fusarium solani, Rhizoctonia solani, Rhizoctonia solani* AG 1 (IB), *Rhizoctonia solani* AG 2—2 (IV), *Phytophthora capsici, Phytophthora parasitica, Sclerotinia sclerotiorum, Sclerotium cepivorum* and *Verticillium dahliae*. In addition, strain WYE 324 also showed strong antagonism against *Pythium graminicola, Fusarium oxysporum, Fusarium solani, Rhizoctonia solani, Rhizoctonia solani* AG 1 (IB), *Rhizoctonia solani* AG 2—2 (IV), *Phytophthora capsici, Phytophthora parasitica, Sclerotinia sclerotiorum*, and *Sclerotium cepivorum*.

EXAMPLE V

Preparation of Antifungal Biocontrol Agent in the Form of Powder

A delivery medium was prepared by mixing wheat bran, chitosan, wood sawdust, chitin, and PHARMAMEDIA according to Table VIII. The delivery medium was pelletized using an extruder. In the process of pelletizing, the degree of pellet formation was determined and recorded as good in the case of good pellet formation without debris and disruption; whereas recorded as poor in the case of poor pellet formation. The results are shown in Table VIII. It was also determined as poor, moderate, and good according to the air penetration and cellular growth of the delivery medium. The results are shown in Table VIII.

One hundred fifty nil of the culture of Streptomnyces sp. WYE 20 or WYE 324 ($10^5$–$10^7$ cfu/ml) obtained in "Materials and Methods" were inoculated into the resulting autoclaved delivery medium and then incubated at 30° C. for 5 to 14 days. The cultures of Streptomyces sp. WYE 20 or WYE 324 in each delivery medium were aseptically harvested and dried in a U.V.-sterilized laminar flow bench. The dried product was aseptically blended to obtain an antifungal biocontrol agent consisting of Streptomyces sp. WYE 20 or WYE 324 and the delivery medium, in the form of powder.

The number of cells of WYE 20 or WYE 324 in the delivery medium was adjusted to $10^5$–$10^{10}$ cfu/g delivery medium. The resulting antifungal biocontrol agent which consisted of WYE 20 or WYE 324 and a delivery medium was kept at 4° C. and 25° C. for 3 months. The viability and growth of WYE 20 or WYE 324 in the delivery medium was determined at intervals of one month and recorded at 3 months.

One gramn of delivery medium containing WYE 20 or WYE 324 was added to 9 ml of sterile distilled water and thoroughly mixed by vortax. The cfu per gram of the resulting suspension was determined by serial-dilution and spread-plate technique and shown in Tables VIII and IX.

TABLE VIII (unit: w/w %)

| Delivery Medium (D.M.) | Wheat bran | Chitosan | Wood sawdust | Chitin | PHARMA MEDIA | Pellet formation | Air penetration | Cellular growth |
|---|---|---|---|---|---|---|---|---|
| D.M. 1 | 65 | 1 | 30 | 2 | 2 | Good | Moderate | Moderate |
| D.M. 2 | 65 | 2 | 30 | 2 | 1 | Good | Moderate | Moderate |
| D.M. 3 | 65 | 2 | 30 | 2 | 1 | Good | Moderate | Moderate |
| D.M. 4 | 65 | 1 | 30 | 1 | 3 | Good | Moderate | Moderate |
| D.M. 5 | 65 | 1 | 30 | 3 | 1 | Good | Moderate | Moderate |
| D.M. 6 | 63 | 5 | 30 | 1 | 1 | Good | Moderate | Moderate |
| D.M. 7 | 60 | 5 | 30 | 2 | 3 | Good | Moderate | Moderate |
| D.M. 8 | 50 | 1 | 45 | 2 | 2 | Good | Good | Good |
| D.M. 9 | 45 | 5 | 45 | 2 | 3 | Good | Good | Good |
| D.M. 10 | 45 | 3 | 50 | 1 | 1 | Good | Good | Good |
| D.M. 11 | 40 | 3 | 55 | 1 | 1 | Good | Good | Good |
| D.M. 12 | 40 | 1 | 55 | 3 | 1 | Good | Good | Good |
| D.M. 13 | 40 | 1 | 55 | 1 | 3 | Good | Good | Good |
| Control 1 | 90 | 2 | 5 | 2 | 1 | Good | Poor | Poor |
| Control 2 | 80 | 5 | 10 | 3 | 2 | Good | Poor | Poor |
| Control 3 | 70 | 3 | 25 | 1 | 1 | Good | Poor | Poor |
| Control 4 | 30 | 5 | 60 | 2 | 3 | Poor | Good | nt |
| Control 5 | 20 | 5 | 70 | 9 | 3 | Poor | Good | nt |
| Control 6 | 10 | 5 | 80 | 2 | 3 | Poor | Good | nt | nt: not tested

TABLE IX (unit: w/w %)

| Delivery Medium (D.M.) | Wheat bran | Chitosan | Wood sawdust | Chitin | PHARMA MEDIA | Initial cell no. of WYE 20 or WYE 324 (cfu/g) | Cell NO. of WYE 20 or WYE 324 after 3 months (cfu/g) at 4° C. | at 25° C. | Cellular growth |
|---|---|---|---|---|---|---|---|---|---|
| D.M. 1 | 65 | 1 | 30 | 2 | 2 | $1.2 \times 10^7$ | $1.0 \times 10^6$ | $2.3 \times 10^5$ | Good |
| D.M. 2 | 65 | 2 | 30 | 1 | 2 | $1.9 \times 10^7$ | $1.5 \times 10^6$ | $2.9 \times 10^5$ | Good |
| D.M. 3 | 65 | 2 | 30 | 2 | 1 | $1.3 \times 10^7$ | $1.4 \times 10^6$ | $2.5 \times 10^5$ | Good |
| D.M. 4 | 65 | 1 | 30 | 1 | 3 | $2.1 \times 10^7$ | $1.7 \times 10^6$ | $3.6 \times 10^5$ | Good |
| D.M. 5 | 65 | 1 | 30 | 3 | 1 | $2.0 \times 10^7$ | $1.2 \times 10^6$ | $3.1 \times 10^5$ | Good |
| D.M. 6 | 63 | 5 | 30 | 1 | 1 | $2.7 \times 10^7$ | $1.1 \times 10^6$ | $2.7 \times 10^5$ | Good |
| D.M. 7 | 60 | 5 | 30 | 2 | 3 | $1.5 \times 10^7$ | $1.3 \times 10^6$ | $3.3 \times 10^5$ | Good |
| D.M. 8 | 50 | 1 | 45 | 2 | 2 | $1.6 \times 10^8$ | $2.1 \times 10^7$ | $2.1 \times 10^6$ | Good |
| D.M. 9 | 45 | 5 | 45 | 2 | 3 | $2.6 \times 10^8$ | $1.1 \times 10^7$ | $2.5 \times 10^6$ | Good |
| D.M. 10 | 45 | 3 | 50 | 1 | 1 | $2.1 \times 10^8$ | $1.0 \times 10^7$ | $3.1 \times 10^6$ | Good |
| D.M. 11 | 40 | 3 | 55 | 1 | 1 | $1.9 \times 10^8$ | $1.6 \times 10^7$ | $3.5 \times 10^6$ | Good |
| D.M. 12 | 40 | 1 | 55 | 3 | 1 | $1.8 \times 10^8$ | $1.9 \times 10^7$ | $2.4 \times 10^6$ | Good |
| D.M. 13 | 40 | 1 | 55 | 1 | 3 | $2.2 \times 10^8$ | $1.3 \times 10^7$ | $1.9 \times 10^6$ | Good |

As shown in Tables VIII and IX, D.M. 1 to 13 were good and moderate in pellet formation, air penetration, and cellular growth, whereas Controls 1 to 6 with a different range of components were poor in pellet formation, air penetration, or cellular growth.

In addition, D.M. 1 to 13 pellets were coated with sporulation medium of YGM and determined the effects on cellular growth and viability. The results are shown in Table X.

TABLE X (unit: w/w %)

| Delivery Medium (D.M.) | Wheat bran | Chitosan | Wood sawdust | Chitin | PHARMA MEDIA | YGM* | Initial cell no. of WYE 20 or WYE 324 (cfu/g) | Cell No. of WYE 20 or WYE 324 after 3 months (cfu/g) at 4° C. | at 25° C. | Cellular growth |
|---|---|---|---|---|---|---|---|---|---|---|
| D.M. 14 | 65 | 1 | 30 | 2 | 2 | 0.2 | $1.1 \times 10^7$ | $1.2 \times 10^6$ | $2.4 \times 10^5$ | Good |
| D.M. 15 | 65 | 2 | 30 | 1 | 2 | 0.5 | $1.4 \times 10^7$ | $1.4 \times 10^6$ | $2.9 \times 10^5$ | Good |
| D.M. 16 | 65 | 2 | 30 | 2 | 1 | 1.0 | $1.6 \times 10^7$ | $1.6 \times 10^6$ | $2.6 \times 10^5$ | Good |
| D.M. 17 | 65 | 1 | 30 | 1 | 3 | 1.5 | $2.0 \times 10^7$ | $1.9 \times 10^6$ | $4.2 \times 10^5$ | Good |
| D.M. 18 | 65 | 1 | 30 | 3 | 1 | 1.8 | $2.2 \times 10^7$ | $1.3 \times 10^6$ | $3.2 \times 10^5$ | Good |
| D.M. 19 | 63 | 5 | 30 | 1 | 1 | 2.0 | $1.7 \times 10^7$ | $2.1 \times 10^6$ | $3.7 \times 10^5$ | Good |

TABLE X-continued (unit: w/w %)

| Delivery Medium (D.M.) | Wheat bran | Chitosan | Wood sawdust | Chitin | PHARMA MEDIA | YGM* | Initial cell no. of WYE 20 or WYE 324 (cfu/g) | Cell No. of WYE 20 or WYE 324 after 3 months (cfu/g) at 4° C. | at 25° C. | Cellular growth |
|---|---|---|---|---|---|---|---|---|---|---|
| D.M. 20 | 60 | 5 | 30 | 2 | 3 | 3.5 | $1.1 \times 10^7$ | $2.3 \times 10^6$ | $3.4 \times 10^5$ | Good |
| D.M. 21 | 50 | 1 | 45 | 2 | 2 | 3.5 | $1.2 \times 10^8$ | $2.3 \times 10^7$ | $2.3 \times 10^6$ | Good |
| D.M. 22 | 45 | 5 | 45 | 2 | 3 | 2.5 | $1.6 \times 10^8$ | $2.1 \times 10^7$ | $2.5 \times 10^6$ | Good |
| D.M. 23 | 45 | 3 | 50 | 1 | 1 | 2.0 | $2.2 \times 10^8$ | $1.3 \times 10^7$ | $3.2 \times 10^6$ | Good |
| D.M. 24 | 40 | 3 | 55 | 1 | 1 | 1.5 | $2.9 \times 10^8$ | $2.1 \times 10^7$ | $3.6 \times 10^6$ | Good |
| D.M. 25 | 40 | 1 | 55 | 3 | 1 | 0.5 | $1.4 \times 10^8$ | $1.9 \times 10^7$ | $2.6 \times 10^6$ | Good |
| D.M. 26 | 40 | 1 | 55 | 1 | 3 | 0.2 | $1.2 \times 10^8$ | $1.3 \times 10^7$ | $2.9 \times 10^6$ | Good |

YGM*: w/w % of total weight.

As shown in Table IX and X, the cells of WYE 20 and WYE 324 were stabilized in D.M. 1 to 26 for a long period of time (>3 months). The cells of WYE 20 and WYE 324 in D.M. 1 to 26 were shown >$10^5$ cfu/g which was required for the biocontrol activity after 3 months storage. In particular, when D.M. 14 to 26 coated with the medium of YGM were used, the stability of the cells of WYE 20 and WYE 324 was improved.

EXAMPLE VI

Preparation of Biocontrol Agents in the Form of Suspension

A delivery medium comprising 20 g of pectin and 2 g of colloidal chitin and the remaining water on the basis of the total volume of 1.0 liter distilled water was autoclaved at 121° C. for 15 minutes. Preparation of a biocontrol agent in the form of suspension was achieved by incorporating Streptomyces sp. WYE 20 or WYE 324 as described in "Materials and Methods", into the resulting autoclaved delivery medium ($1.2 \times 10^7$ cfu/ml).

The resulting product was kept at 4° C. The form of biocontrol agent was suitable for the treatment of plant seeds and seedling beds by in-furrow application, or spraying after dilution with water.

EXAMPLE VII

Antifungal Activity Assay

In vivo biocontrol assays were carried out to determine the efficacy of biocontrol agents prepared in Example V and Example VI. The biocontrol agents were tested for their ability to reduce fungal diseases and enhance plant growth by treating plants, plant seeds, plant roots, seedling beds, pots, potting mixtures, or soil.

(1) Biocontrol Activity to Rhizoctonia Damping-off of Cucumber (*Cucumis sativus* L.).

A biocontrol assay was carried out to test the efficacy of WYE 20 as a biocontrol agent in inhibiting Rhizoctonia damping-off of cucumber.

Cucumber seeds were treated with 20 ml of WYE 20 ($1.2 \times 10^7$ cfu/ml) prepared in Example VI by immersing seeds therein for three hours and then being seeded in pots. Seeds were immersed for three hours in sterilized distilled water and a delivery medium, respectively; each resulting seed was used as a control.

Hortus (England) was used as a potting mixture. The potting mixture was autoclaved at 121° C. for 60 minutes, and placed for 12 hours at 25° C., and then autoclaved at 121° C. for 60 minutes again. This autoclaving cycle was repeated three times.

*Rhizoctonia solani* was cultured on PDB (Potato dextrose broth: DIFCO) at 25° C. for 14 days, harvested and mixed with autoclaved potting mixture so as to obtain an approximately 60% disease incidence. The cucumber seeds were treated with biocontrol agent and each control seed was seeded in pots containing the potting mixture into which *Rhizoctonia solani* had been artificially inoculated.

Disposable paper cups (diameter of 9 cm) were used as seedling pots. Six cups containing three seeds per cup were prepared in each test. The cups were placed in a random block design in a glasshouse. Moisture was kept between 40% and 60% and additional water was supplied as needed. The temperature was maintained between 25° C. and 30° C. in daylight.

The results of emergence and occurrence of damping-off were periodically recorded. The final results are shown in Table XI.

TABLE XI

| Treatments | No. of Cucumber Seeds | Emerged Cucumber Seeds (%) 7 days | Healthy Plants (%) 14 days | Fresh Weight (g)/above ground 18 days |
|---|---|---|---|---|
| No pathogen + control | 18 | 18b[x] (100) | 18b[x] (100) | 2.61b[x] |
| *Rhizoctonia solani* + control | 18 | 7a (39) | 7a (39) | 1.73a |
| *Rhizoctonia solani* + Liquid D.M. treatment | 18 | 8a (44) | 8a (44) | 1.75a |
| *Rhizoctonia solani* + Liquid D.M. of WYE 20 | 18 | 18b (100) | 18b (100 | 2.51b |

[x]Means in a column followed by the same letter are not significantly different at the P = 0.05 level. D.M.: Delivery Medium.

As shown in Table XI, cucumber seeds treated with WYE 20 in delivery medium as a biocontrol agent did not show Rhizoctonia damping-off of cucumber. In addition, cucumber plants from control seeds showed severe growth retardation resulting from *Rhizoctonia solani*, whereas plants from treated seeds did not. The results showed that WYE 20 was effective in controlling *Rhizoctonia solani* and in enhancing plant growth.

(2) Biocontrol Activity Against Powdery Mildew of Cucumber (*Cucumis sativus* L.).

A biocontrol assay was carried out to test the efficacy of WYE 324 ($1.2 \times 10^7$ cfu/ml) in the biocontrol agent prepared in Example VI in inhibiting powdery mildew of cucumber plants in pots.

Disposable paper cups (diameter of 9 cm) were used as seedling pots. One cucumber seed was seeded in each cup containing potting mixture consisting of agricultural field soil and Hortus (England) (4:1 v/v ratio). The cups were placed in a glasshouse. Additional water was supplied as needed and the temperature was maintained between 25° C. and 30° C. in daylight.

Twenty ml of the biocontrol agent containing WYE 324 were sprayed on one cucumber plant (14-day-old) at the beginning of the assay and sprayed one more time after a week. Plants sprayed with the same amounts of water were used as a control. Three cucumber plants (one cucumber plant per cup) of each treated group and the control group were prepared in the assay.

To naturally induce powdery mildew of cucumber caused by *Sphaerotheca fuliginea*, three cups per group and three diseased cucumber plants (one plant per cup) were used and set in a random block arrangement in a glasshouse. Moisture was kept between 70% and 90% and additional water was supplied as needed. The temperature was maintained between 25° C. and 30° C. in a glasshouse. The incidence of cucumber powdery mildew was investigated. The experiment was continued for 2 weeks and the assay was repeated. The results are shown in Table XII.

TABLE XII

| Treatments | Incidence of Powdery Mildew of Cucumber | |
|---|---|---|
| | Experiment 1 | Experiment 2 |
| Control | + | + |
| WYE 324 Treated | − | − |

As shown in Table XII, powdery mildew was not detected in cucumber plants sprayed with the biocontrol agent containing WYE 324; whereas the disease was observed in control plants. The results showed that WYE 324 was effective in controlling powdery mildew of cucumber (*Cucumis sativus* L.).

(3) Biocontrol Activity of Streptomyces sp. WYE 20 or WYE 324 to Rhizoctonia Brown Patches of Golf Green Creeping Bentgrass A biocontrol assay was carried out to test the efficacy of Streptomyces sp. WYE 20 and WYE 324 in inhibiting Rhizoctonia brown patch of golf green creeping bentgrass.

Streptomyces sp. WYE 20 and WYE 324 produced by liquid culture as described in "Materials and Methods" above were used in this assay. The cell number of Streptomyces sp. WYE 20 or WYE 324 was adjusted to $2.0 \times 10^5$ cfu/ml. The assay was carried out on each block treated with WYE 20 or WYE 324, or control. Four blocks (1.5 m×1.5 m) of each treated group and control group were prepared on a golf green. The assay was carried out in a random block design. Strain WYE. 20 or WYE 324 was sprayed every 7–10 days in the experimental blocks from Jun. 25, 1996 to Aug. 23, 1996. Two and a half liters of WYE 20 or WYE 324 per block were used each time; whereas the control blocks were provided with the same amount of water. No chemical fungicides were used in the experimental period. The incidence of Rhizoctonia brown patches was periodically recorded and shown in Table XIII (Site 1) and Table XIV (Site 2).

As shown in Table XIII (Site 1) and Table XIV (Site 2), the incidence of Rhizoctonia brown patches was dramatically reduced in blocks treated with WYE or WYE 324. The results showed that WYE 20 and WYE 324 were effective in inhibiting Rhizoctonia brown patches of golf green creeping bentgrass.

TABLE XIII (Site 1)

| | Incidence of Rhizoctonia Brown Patches (%) | | |
|---|---|---|---|
| Treatments | 7/25/96 | 8/6/96 | 8/23/96 |
| Control | $10.18a^x$ | $14.6a^x$ | $59a^x$ |
| WYE 20 treated | 3.38b | 9.2b | 24b |
| WYE 324 treated | 0.00c | 5.2c | 24b |

$^x$Means in a column followed by the same letter are not significantly different at the P = 0.05 level.

TABLE XIV (Site 2)

| | Incidence of Rhizoctonia Brown Patches (%) | | |
|---|---|---|---|
| Treatments | 7/25/96 | 8/6/96 | 8/19/96 |
| Control | $5.6a^x$ | $9.3a^x$ | $28.3a^x$ |
| WYE 20 treated | 0.0b | 0.8b | 5.3b |
| WYE 324 treated | 0.0b | 0.0b | 0.7c |

$^x$Means in a column followed by the same letter are not significantly different at the P = 0.05 level.

(4) Biocontrol Activity to Rhizoctonia Large Patches of a Fairway Turfgrass (*Zoysia japonica*).

A biocontrol assay was carried out to test the efficacy of biocontrol agents including Streptomyces sp. WYE 20 or strain IBT 678 prepared in Example VI in inhibiting Rhizoctonia large patches of fairway turfgrass (*Zoysia japonica*). The cell number of Streptomyces sp. WYE 20 or strain IBT 678 in a biocontrol agent was adjusted to $2.0 \times 10^6$ cfu/ml.

Soils infested with *Rhizoctonia solani* AG 2—2 were inoculated into a fairway turfgrass (*Zoysia japonica*) and then planted in pots (diameter of 25 cm).

Two hundred ml of the biocontrol agent were treated once per week for two weeks and three weeks in 1996 and 1997, respectively. Pots treated with the same amounts of water were used as a control group. Three pots per group were used and set in a random block arrangement. To naturally induce disease, the pots were placed near the fairway of a golf course from the beginning of September to the beginning of October, 1996 as well as from the beginning of March to the end of June, 1997, respectively. The incidence of Rhizoctonia large patches was investigated. Large patches were not detected in pots treated with the biocontrol agent containing WYE 20; whereas the disease was observed in control and IBT 678 treated pots as shown in Table XV.

TABLE XV

| | Incidence of Large patches of *Zoysia japonica* | |
|---|---|---|
| Treatments | Fall 1996 | Spring 1997 |
| Pathogen + Control | + | + |
| Pathogen + WYE 20 Treated | − | − |
| Pathogen + IBT 678 Treated | Not tested | + |

As shown in Table XV, the results showed that WYE 20 was effective in controlling Rhizoctonia large patches of a fairway turfgrass (*Zoysia japonica*).

(5) Biocontrol Activity Against Phytophthora Blight of Pepper Plant(*Capsicum annuum* L.)

A biocontrol assay was carried out to test the efficacy of WYE 20 or WYE 324 in the biocontrol agent of Example VI in inhibiting Phytophthora blight of pepper seedlings in pots.

Pepper seeds were submerged in sterilized water for 2 days and treated with WYE 20 or WYE 324 in the biocontrol agent of Example VI by submerging them for 18 hours (treating group). The cell numbers of Streplonmyces sp. WYE 20 and WYE 324 were adjusted to $1.2 \times 10^7$ cfu/ml and $1.7 \times 10^7$ cfu/ml, respectively. Pepper seeds were submerged in sterilized water for 2 days and then for 18 hours. They were used as a control group. On the other hand, pepper seeds submerged in sterilized water for 2 days were replaced in the delivery medium of Example VI for 18 hours. They were used as the other control group.

As described in the assay with cucumber above, *Phytophthora capsici* cultured in PDB (Potato dextrose broth: Difco) at 25° C. for 14–21 days was harvested and inoculated into a sterilized potting mixture (Hortus, England) to obtain an infested potting mixture with a disease incidence of 80% of Phytophthora blight for control pepper seedlings. The resulting potting mixture infested with *Phytophthora capsici* was used to determine the efficacy of WYE 20 or WYE 324 in the delivery medium in inhibiting phytophthora blight of pepper seedlings in the assay.

Disposable paper cups (diameter of 9.0 cm) were used as seedling pots. Fourteen cups containing three seeds per cup were prepared in each test. Experiments were performed in a glasshouse at a temperature of 25° C. to 32° C. in daylight. In the glasshouse, pots were set in a random block arrangement. The moisture was maintained at 80% and additional water was sprayed on the top of the pots as needed.

The emergence and incidence of Phytophthora blight of pepper plants were recorded as shown in Table XVI.

TABLE XVI

| Treatments | No. of Planted Pepper Seeds | No. of Emerged Pepper Seeds (Emergence: %) 14 days | Pepper seedlings showing Phytophthora blight (disease incidence: %) 14 days | Pepper seedlings showing Phytophthora blight (disease incidence: %) 18 days |
| --- | --- | --- | --- | --- |
| No pathogen + Control | 42 | 37(88a$^x$) | 0(0c$^x$) | 0(0c$^x$) |
| *Phytophthora capsici* + Control | 42 | 34(81a) | 28(82a) | 33(97a) |
| *Phytophthora capsici* + liquid D.M. Treated | 42 | 35(83a) | 29(83a) | 34(97a) |
| *Phytophthora capsici* + WYE 20 Treated | 42 | 34(81a) | 12(35b) | 26(76b) |
| *Phytophthora capsici* + WYE 324 Treated | 42 | 36(86a) | 22(61c) | 28(78b) |

$^x$Means in a column followed by the same letter are not significantly different at the P = 0.05 level.

As shown in Table XVI, there was a significant reduction in Phytophthora blight of pepper plants in the seeds treated with WYE 20 or WYE 324 as compared to the control group. The result showed that WYE 20 and WYE 324 of the present invention were effective in controlling Phytophthora blight of pepper plants.

(6) An Assay to Determine Plant Growth Enhancement Using Pepper Seedlings

A seedling assay was carried out to determine the efficacy of WYE 20 and WYE 324 in a biocontrol agent of the present invention in enhancing the growth of pepper plants.

Pepper seeds submerged in sterilized water for 2 days were treated with WYE 20 or WYE 324 in a biocontrol agent as prepared in Example V (D.M. 22) (1000 seeds per 4 g biocontrol agent). The cell numbers of Streptomyces sp. WYE 20 and WYE 324 prior to seed treatment were adjusted to $1.2 \times 10^-$ cfu/ml and $1.7 \times 10^7$ cfu/ml, respectively. Pepper seeds were submerged in sterilized water and used as a control group (Control 1). Meanwhile, pepper seeds were treated with the delivery medium (1000 seeds per 4 g D.M.22) not containing WYE 20 or WYE 324 and used as the other control group (Control 2).

The planting of the pepper seeds was carried out in the same way as the cucumber seedlings shown above.

Disposable paper cups (diameter of 9.0 cm) were used as seedling pots. One hundred and twenty one cups containing one seed per cup were prepared in each test. Experiments were performed in a glasshouse at a temperature of 25° C. to 32° C. in daylight. In the glasshouse, pots were set in a random block arrangement. The moisture was maintained in a range of 40% to 60% and additional water was sprayed on the top of the pots as needed. Fifteen ml of cell culture broth of WYE 20 or WYE 324 obtained in "Materials and Methods" were inoculated into the seedling pot treated with the biocontrol agent after 4 weeks of cultivation. The same amount of water was applied to the control groups. The experiments were continued for 9 weeks and the results were shown in Table XVII.

TABLE XVII

| Treatments | Pepper Seedlings | Plant Height (cm) (average) |
| --- | --- | --- |
| Control 1 | 121 | 23.7a$^x$ |
| Control 2 | 121 | 24.5a |
| WYE 20 Treated | 121 | 27.4b |
| WYE 324 Treated | 121 | 28.6b,c |

$^x$Means in a column followed by the same letter are not significantly different at the P = 0.05 level.

As shown in Table XVII, there was a significant enhancement in the growth of the plants from the pepper seeds treated with WYE 20 or WYE 324 as compared to those plants germinated from control seeds. This indicates that WYE 20 or WYE 324 of the present invention is highly effective in enhancing the growth of pepper plants.

(7) A Biocontrol Assay Using Pepper Seedlings in Agricultural Fields

A biocontrol assay was carried out to determine the efficacy of a biocontrol agent of the present invention for controlling Phytophthora blight and for enhancing plant growth in agricultural fields.

Pepper seeds submerged in sterilized water for 2 days were immersed in a biocontrol agent prepared in Example VI for 3 hours. The seeds were treated with a biocontrol agent (D.M.22) (1,000 seeds per 4 g) prepared in Example V. The cell numbers of Streptomyces sp. WYE 20 and WYE 324 prior to seed treatment were adjusted to $1.2 \times 10^7$ cfu/ml and $1.7 \times 10^7$ cfu/ml, respectively.

Pepper seeds were submerged in sterilized water for 2 days and 3 hours again. Thus the pepper seeds were treated with the same delivery medium not containing WYE 20 or WYE 324 and used as a control group. Each seed was planted in seedling beds. Water was sprayed as needed and a temperature of between 20° C. and 35° C. was maintained. When seedlings were grown to 1.5 to 2.0 cm in height, the pepper seedlings were transplanted into a seedling tray consisting of 25 seedling holes (5 cm×5 cm, 6 cm depth) containing a mixture of fine sandy potting soil and WYE 20 or WYE 324 in the delivery medium (0.1 g per seedling hole). Control pepper seedlings were transplanted into seedling holes containing the same amount of sandy potting soil and the same amount of delivery medium only. These seedling pots were incubated in a greenhouse at a temperature of 18° C. to 35° C. and additional water was supplied as needed. In the greenhouse, pots were set in a random block arrangement. After 11 weeks of growth in the greenhouse, each plant was transplanted to agricultural fields. Before a week of transplantation, 10 ml culture broth of WYE 20 or WYE 324 ($1.2$–$1.7 \times 10^5$ cfu/ml) were added per seedling hole of treating group. The same amount of water was supplied to control seedling pots.

The disease incidence and the growth of the transplanted peppers were observed periodically and the mean was recorded as shown in Table XVIII (Field 1) and XIX (Field 2).

TABLE XVIII (Field 1)

| Treatments | No. of Transplanted Pepper Plants | Plant Height (cm) at 62 days after transplantation | Incidence of phytophthora Blight (%) | |
|---|---|---|---|---|
| | | | 62 days after transplantation | 101 days after transplantatin |
| Control | 1.340 | 78.5a$^x$ | 28.4a$^x$ | 98.6a$^x$ |
| WYE 20 Treated | 1.340 | 86.0b | 23.5b | 89.2b |
| WYE 324 Treated | 1.340 | 90.5c | 8.7c | 76.1c |

$^x$Means in a column followed by the same letter are not significantly different at the $P = 0.05$ level.

TABLE XIX (Field 2)

| Treaments | No. of Transplanted Pepper Plants | Incidence of Phytophthora Blight (%) | |
|---|---|---|---|
| | | 82 days after transplantation | 101 days after transplantation |
| Control | 860 | 26a$^x$ | 42.4a$^x$ |
| WYE 20 Treated | 860 | 0b | 7.6b |
| WYE 324 Treated | 860 | 0b | 2.0c |

$^x$Means in a column followed by the same letter are not significantly different at the $P = 0.05$ level.

As shown in Table XVIII and XIX, there was a significant enhancement in the growth and reduction of Phytophthora blight in the plants from the pepper seeds treated with WYE 20 or WYE 324 as compared to those plants germinated from control seeds. This indicates that WYE 20 and WYE 324 of the present invention are highly effective in controlling Phytophthora blight and in enhancing plant growth of pepper in agricultural fields.

Having provided exainples of embodiments of the present invention and preferred embodiments, it will be apparent to those skilled in the art that changes and modifications may be made without departing from the present invention and its broader aspects. Therefore, numerous variations, modifications, and embodiments are to be regarded as being within the true spirit and scope of the present invention.

REFERENCES

ATCC Catalogue of Bacteria and Bacteriophages, 17th edition. 1989. American Type Culture Collection, Rockville, Md.

Crawford, D. L., J. M. Lynch, J. M. Whippsw, and M. A. Ousley. 1993. Isolation and characterization of actinomycete antagonists of a fungal root pathogen. Appl. Environ. Microbiol. 59:3899–3905.

Hsu, S. C., and J. L. Lockwood. 1975. Powdered chitin agar as a selective medium for enumeration of actinomycetes in water and soil. Applied Microbiology. pp. 422–426.

Kannwischer, M. E., and Mitchell, D. J. 1978. The influence of a fungicide on the epidemiology of black shank of tobacco. Phytopathology 68:1760–1765.

Locci, R. 1989. Streptomycetes and Related Genera. In Bergeys' Manual of Systematic Bacteriology, Williams and Wilkens, Baltimore, Md. 4:2451–2492.

Pridham, T. G., and D. Gottlieb. 1948. The utilization of carbon compounds by some actinomycetales as an aid for species determination. J. Bacteriol. 56:107–114.

Reddi, G. S., and A. S. Rao. 1971. Antagonism of soil actinomycetes to some soil borne plant pathogenic fungi. Indian Phytopathol. 24:649–657.

Stanghellini, M. E., and J. G. Hancock. 1970. A quantitative method for the isolation of Pythium ultimum from soil. Phytopathology. 60:551–552.

Stasz, T. E., G. E. Harman and G. A. Marx. 1980. Time and site of infection of resistant and susceptible germinating per seeds by *Pythium ultimum*. Phytopathology. 70:730–733.

Suh, H. W. 1992. Production of antifungal compounds by *Pisolithus tinctorius* SMF and Streptomyces sp. WYEC 108, and their role in biological control. Ph.D. Dissertation. University of Idaho, Moscow, Id., USA.

Williams et al. 1983. A probability matrix for identification of Streptomyces. J. Gen. Micorbiol. 129:1815–1830.

Williams et al. 1983. Numerical classification of Streptomyces and related genera. J.Gen. Microbiol. 129:1743–1813.

| U.S. PATENT DOCUMENTS | | |
|---|---|---|
| 4,534,965 | 8/1985 | Brown et al. |
| 4,595,589 | 6/1986 | Tahvonen, Risto |
| 4,668,512 | 5/1987 | Lewis et al. |
| 5,391,493 | 2/1995 | Signorini et al. |
| 5,403,584 | 5/1995 | Crawford et al. |

| FOREIGN PATENT DOCUMENTS | | |
|---|---|---|
| 2524486 | 10/1983 | France |
| WO93/18135 | 9/1993 | World International Property Organization |

OTHER PUBLICATIONS

Bric et al., "Rapid in situ assay for indoleacetic acid production by bacteria immobilized on a nitrocellulose membrane," Appl. Environ. Microbiol. 57:535–538 (1991).

Bruhlmann et al., "Pectinolytic enzymes from actinomycetes for the degumming of ramie bast fibers." Appl. Environ. Microbiol. 60:2107–2112 (1994).

M. L. Lahdenpera., "The control of Fusarium wilt on carnation with a Streptomyces preparation," Acta Horticulturae 216:85–92 (1987).

Ames, "Mycorrhiza development in onion in response to inoculation with chitin-decomposing actinomycetes," New Phytol. 112:423–427 (1989).

Bolton, "Effects of amending soilless growing mixtures with soil containing antagonistic organisms on root rot and blackleg of geranium (*Pelargonium Hortorum*) caused by *Phythium splendens*," Can. J. Plant Sci. 58:379–383 (1978).

Bolton, "Control of *Pythium aphanidermatum* in pointsettia in a soilless culture by *Trichoderma viride* and a *Streptomyces sp.*," Can. J. of Plant pathology 2:93–95 (1980).

Broadbent et al., "Bacteria dn Actinomycetes antagonistic to fungal root pathogens in Australian soils," Aust. J. Biol. Sci. 24:925–944 (1971).

DeFrank and Putnam, "Screening procedures to identify soilborne actinomycetes that can produce herbicidal compounds," Weed Science 33:271–274 (1985).

Filnow and Lockwood, "Evaluation of several actinomycetes and the fungus *Hypochytrium catenoides* as biocontrol agents for Phytophthora root rot of soybean," Plant Dis. 69:1033–1036 (1985).

Fravel et al., "Encapsulation of potential biocontrol agents in an alginate-clay matrix," Phytopathology 75:774–777 (1985).

Hussain et al., "Biological control of *Macrophomina phaseolina* charcoal rot of sunflower and mung bean," J. Phytopathology 130:157–160 (1990).

Kobayashi, et al., "Pironetin, a novel plant growth regulator from Streptomyces sp.," Abstract S2-3, p34, BMP Japan 95, Apr. 23–26. Oiso, Kanagawa, Japan (1995).

Lahdenpera et al., "Mycostop-A novel biofungicide based on Streptomyces bacteria," published prior to 1991.

Leong, "Siderophores: their biochemistry and possible role in the biocontrol plant pathogens," Annu. Rev. Phytopathol. 24:187–209 (1986).

Liljeroth et al., "Assimilate translocation to the Rhizosphere of two wheat lines and subsequent utilization by rhizosphere microorganisms at two soil nitrogen concentrations," Soil Biol. Biochem. 22:1015–1021 (1990).

Marcos et al., "Effect of compost on rhizosphere microflora of the tomato and on the incidence of plant growth-promoting rhizobacteria (PGPR)," Appl. Environ. Microbiol. 61:194–199 (1995).

Merriman et al., "Effect of Bacillus and Streptomyces spp. applied to seed," In E. Bruehl (ed.), Biology and control of soilborne plant pathogens, pp. 130–133 (1977).

Meyer and Linderman, "Selective influence on populations of rhizosphere or rhizoplane bacteria and actinomycetes by mycorrhizas formed by *Glomus fasciculatum*," Soil Biol. Biochem. 18:191–196 (1986).

Miller et al., "Variation and composition of bacterial populations in the rhizospheres of maize, wheat, and grass cultivars," Can. J. Microbiol. 35:656–660 (1989).

Miller et al., "Fluctuations in the fluorescent pseudomonas and actinomycete populations of rhizosphere and rhizoplane during the growth of spring wheat," Can. J. Microbiol. 36:254–258 (1989).

Miller et al., "The dynamics of actinomycetes and fluorescent Pseudomonads in wheat rlizoplane and rhizosphere," Symbiosis 9:389–391 (1982).

Panosyan et al., "The nature of physiologically active substances of actinomycetes and the effect of their metabolites on plant growth," Plant Microbe Relationships, pp. 241–245 (1965).

Scrinivansan et al., "Physiology, and nutritional aspects of actinomycetes": an overview," World Journal of Microbiology and Biotechnology 7:171–184 (1991).

Singh and Mehrota, "Biological control of *Rhizoctonia bataticola* on gram by coating seed with Bacillus and Streptomyces spp. and their influence on plant growth." Plant and Soil 56:475–483 (1980).

Stevenson, "Antibiotic activity of actinomycetes in soil as demonstrated by direct observation techniques," J. Gen. Microbiol. 15:372–380 (1956).

Sutherland and Papavizas, "Evaluation of oospore hyperparasites for the control of Phytophthora crown rot of pepper," J. Phytopathology 131:33–39 (1991).

Tahvonen, "Preliminary experiments into the use of Streptomyces spp. isolated from peat in the biological control of soil and seed-borne diseases in peat culture," Journal of the Scientific Agricultural Society of Finland 54:357–369 (1982).

Tahvonen, "Mycostop-ettbiologiski bekampningsmedel mot svampsjukdomar," (Mycostop, biological formulation for control of fungal diseases), Vaxtskyddsnotiser 49:86–90. English summary only (1985).

Tahvonen and Avikainen, "The biological control of seed-borne *Aternaria brassicicola* of cruciferous plants with a powdery preparation of Streptomyces sp.," Journal of Agricultural Science in Finland 59:199–207 (1987).

Tu, "Hyperparasitism of *Streptomyces albus* on a destructive mycoparasite nectria inventa," J. Phytopathology 117:71–76 (1986).

Turhan, "A new race of *Streptomyces ochraceisclerolicus* in the biological control of some soilborne plant pathogens," Journal of Plant Diseases and Protection 88:422–434 (1981).

Turhan and Turhan "Suppression of damping-off pepper caused by *Pythium ulimum* Trow and *Rhizoctonia solani* Kuhn by some new antagonists in comparison with *Trichoderma harzianum* Rifai," J. Phytopathology 126:175–182 (1989).

Zuberer et al., "Populations of bacteria and actinomycetes associated with sclerotia of *Phymatotrichum omnivorum* buried in Houston black clay," Plant and Soil 112:69–76 (1988).

Warren et al., "Rheologies and morphologies of three actinomycetes in submerged culture," Biotechnology and Bioengineering 45:80–85 (1995).

Shahab et al., "Cell physiology and antibiotic production of *Streptonzyces coelicolor* grown on solid medium," Biotechnology Letter 16:1015–1020 (1994).

Fukuchi et al., "Rotihibins, novel plant growth regulators from *Streptomyces graminofaciens*." The Journal of Antibiotics 48:1004–1010 (1995).

Liu et al., "Biological control of potato scab in the field with antagonistic *Streptomyces scabies*," Phytopathology 85:827–831(1995).

Bowers et al., "Influence of disease-suppressive strains of Streptomyces on the native Streptomyces community in soil as determined by the analysis of cellular fatty acids," Can. J. Microbiol. 42:27–37 (1996).

Bayer and Diekmann, "The chitinase system of Streptomyces sp. ATCC 11238 and its significance for fingal cell wall degradation," Appl. Microbiol. Biotechnol. 23:140–146 (1985).

Lorito et al., "Synergistic interaction between fungal cell wall degrading enzymes and different antifungal compounds enhances inhibition of spore germination.," Microbiology .140:623–629 (1994).

Mahadevan and Crawford, "Properties of the chitinase of the antifungal biocontrol agent *Streptomyces lydicus* WYEC 108," Enzyme Microbial Technol. (1996). In press.

Mohamed, "Physiological and antagonistic activities of Streptomycetes in rhizosphere of some plants," Egypt. J. Phytopathol. 14:121–128 (1982).

Sardi et al., "Isolation of endophytic Streptomyces strains from surface-sterilized roots," Appl. Environ. Microbiol. 58:2961–2963 (1992).

Sneh et al., "Parasitism of oospores of *Phytophihora megasperma* var sojae *P. cactorum*, Pythium sp., and *Aphanomyces euteiches* in soil by oomycetes, chytridiomycetes, hyphomycetes, actinomycetes, and bacteria," Phytopathology 67:622–628 (1977).

Yuan and Crawford, "Characterization of *Streptomyces lydicus* WYEC 108 as a potential biocontrol agent against fungal root and seed rots," Appl. Environ. Microbiol. 61:3119–3128 (1995).

Fravel, "Role of antibiosis in the biocontrol of plant disease," Annu. Rev. Phytopathol. 26:75–91 (1988).

evalier, "Actinomycetes in agriculture and forestry," P.327–358. In M. Goodfellow, S. T. Wiliams, and M. Mordarski (ed.), Actinomycetes in biotechnology. Academic Press, New York (1989).

Merriman et al., "The effect of inoculation of seed with antagonists of *Rhizoctonia solani* on the growth of wheat," Austr. J. Agr. Res. 25:213–218 (1974).

Merriman et al., "Effect of seed inoculation with *Bacillus subtilis* and *Streptomyces griseus* on the growth of cereals and carrots," Austr. J. Agr. Res. 25:219–226 (1974).

Sivasithamparam and Parker, "Effects of certain isolates of bacteria and actinomycetes on *Gaeumannomyces graminis*, var, tritici and take-all of wheat," Austr. J. Bot. 26:773–782 (1978).

Suslow, "Role of root colonizing bacteria in plant growth. In Phytopathogenic Prokaryotes," ed. M. S. Mount, G. H. Lacy. 1:187–223. London Academic Press (1982).

David and Thomashow, "Current challenges in introducing beneficial microorganisms into the rhizosphere," pp. 1–18 (198).

Jones and Samac, "Biological control of fungi causing alfalfa seedling damnping-off with a disease-suppressive strain of Streptomyces," Biological Control 7:196–204 (1996).

Lee and Rho, "Characteristics of spores formed by surface and submerged cultures of *Streptomyces albidoflavus* SMF301," J. of Gen. Microbiol. 139:3131–3137 (1993).

What is claimed is:

1. A biologically pure culture of at least one microorganism selected from the group consisting of Streptomyces sp. strain KCTC 0341BP and Streptomyces sp. strain KCTC 0342BP.

2. An antifungal biocontrol agent comprising at least one microorganism selected from the group consisting of a biologically pure culture of Streptomyces sp. strain KCTC 0341BP and a biologically pure culture of Streptomyces sp. strain KCTC 0342BP, and a delivery medium.

3. A biologically pure culture of claim 1 or an antifungal biocontrol agent of claim 2, wherein the culture or agent inhibits growth of the fungal phytopathogens *Pythium ultimum, Pythium graminicola, Rhizoctonia solani, Rhizoctonia solani* AG 1 (IB), *Rhizoctonia solani* AG 2—2 (IV), *Fusarium oxysporum, Fusanum solani, Phytophthora capsici, Phytophthora parasitica, Sclerotinia sclerotiorum, Sclerotium cepivorum*, or *Verticillium dahiae*.

4. The culture or agent of claim 3, wherein the culture or agent is used to treat seed-rot, damping-off, root rot, powdery mildew of cucumber, Phytophthora blight of pepper, or Rhizoctonia brown patches of turfgrasses.

5. The antifungal biocontrol agent of claim 2 wherein the delivery medium consists of 40 to 65 w/w % of wheat bran, 1 to 5% of chitosan, 30 to 55 w/w % of wood sawdust, 1 to 3 w/w % of chitin, and 1 to 3 w/w % of cottonseed flour on the basis of the total weight of the delivery mediuim.

6. The antifungal biocontrol agent of claim 5 wherein the delivery medium further consists of 0.2 to 3.5 w/w % of sporulation medium.

7. The antifungal biocontrol agent of claim 5 or 6 wherein the biologically pure culture of Streptomyces sp. strain KCTC 0341BP or Streptomyces sp. strain KCTC 0342BP comprises $10^5$–$10^{10}$ colony forming units per gram of the delivery medium.

8. The antifungal biocontrol agent of claim 2 wherein the delivery medium consists of 1.0 to 3.0 w/w % of pectin and 0.1 to 0.6 w/w % of colloidal chitin in water.

9. The antifungal biocontrol agent of claim 8 wherein the biologically pure culture of Streptomyces sp. strain KCTC 0341BP or Streptomyces sp. strain KCTC 0342BP comprises $10^5$–$10^{10}$ colony forming units per gram of the delivery medium.

10. A method of manufacturing an antifungal biocontrol agent comprising the steps of (a) incubating the cells of Streptomyces sp. strain KCTC 0341BP or Streptomyces sp. strain 0342BP with shaking at 130 rpm to 300 rpm at 25° C. to 33° C.;

(b) harvesting the cells;

(c) lyophilizing the pure culture of Streptomyces sp. strain KCTC 0341BP or Streptomyces sp. strain KCTC 0342BP; and (d) mixing the lyophilized product of step (c) into a delivery medium.

11. The method of claim 10 wherein the delivery medium is 40 to 65 w/w % of wheat bran, 1 to 5 w/w % of chitosan, 30 to 55 w/w % of wood sawdust, 1 to 3 w/w % of chitin, and 1 to 3 w/w % of cottonseed flour on the basis of the total weight of the delivery medium.

12. A method of manufacturing an antifungal biocontrol agent comprising the steps of:

(a) preparing a delivery medium consisting of 40 to 65 w/w % of wheat bran, 1 to 5 w/w % of chitosan, 30 to 55 w/w % of wood sawdust, 1 to 3 w/w % of chitin, and 1 to 3 w/w % of cottonseed flour on the basis of the total weight of the delivery medium;

(b) autoclaving the resulting delivery medium;

(c) mixing at least one biologically pure culture of Streptomyces sp. strain KCTC 0341BP or Streptomyces sp. strain KCTC 0342BP with the delivery medium prepared in step (b);

(d) incubating the cells of Streptomyces sp. strain KCTC 0341BP or Streptomyces sp. strain KCTC 0342BP at 25° C. to 33° C. for 5 to 14 days; and (e) aseptically drying the resulting antifungal biocontrol agent in a UV light-sterilized laminar flow bench at room temperature.

13. The method of manufacturing an antifungal biocontrol agent according to claim 12, wherein step (e) comprises aseptically blending the dried antifungal biocontrol agent.

14. The method of manufacturing an antifungal biocontrol agent according to claim 12, wherein the delivery medium described in step (a) is pelletized, and the resulting pellets are coated with 0.2 to 3.5 w/w % of porulation medium on the basis of the total weight of the delivery medium.

15. The method of manufacturing an antifungal biocontrol agent according to claim 12, wherein the biologically pure culture of Streptomyces sp. strain KCTC 0341BP or Streptomyces sp. strain KCTC 0342BP comprises $10^5$–$10^{10}$ colony forming units per gram of delivery medium.

16. A method of manufacturing an antifungal biocontrol agent comprising the steps of:

(a) preparing a delivery medium consisting of 1.0 to 3.0 w/w % of pectin and 0.1 to 0.6 w/w % of colloidal chitin in water;

(b) autoclaving the resulting delivery medium; and (c) mixing at least one biologically pure culture of Streptomyces sp. strain KCTC 0341BP or Streptomyces sp. strain KCTC 0342BP with the delivery medium prepared in step (b).

17. The method of claim 16 wherein the biologically pure culture of Streptomyces sp. strain KCTC 0341BP or Streptomyces sp. strain KCTC 0342BP added in step (c) comprises $10^5$–$10^{10}$ colony forming units per gram of delivery medium.

* * * * *

UNITED STATES PATENT AND TRADEMARK OFFICE
CERTIFICATE OF CORRECTION

PATENT NO. : 6,280,719 B1
DATED : August 28, 2001
INVENTOR(S) : Hyung-Won Suh

Page 1 of 1

It is certified that error appears in the above-identified patent and that said Letters Patent is hereby corrected as shown below:

<u>Title page,</u>
ABSTRACT, line 8, "canies" should read -- carries --.

<u>Column 29, claim 3,</u>
Line 67, "Fusanum" should read -- Fusarium --.

<u>Column 30, claim 3,</u>
Line 2, "dahiae" should read -- dahliae --.

<u>Column 30, claim 5,</u>
Line 11, "mediuim" should read -- medium --.

<u>Column 31, claim 14,</u>
Line 2, "porulation" should read -- sporulation --.

Signed and Sealed this

Nineteenth Day of March, 2002

Attest:

JAMES E. ROGAN
*Attesting Officer*     *Director of the United States Patent and Trademark Office*